(12) United States Patent
Xu et al.

(10) Patent No.: US 11,512,259 B2
(45) Date of Patent: Nov. 29, 2022

(54) PROCESS FOR PRODUCING LIGHT OLEFINS AND LOW-SULFUR FUEL OIL COMPONENTS

(71) Applicants: CHINA PETROLEUM & CHEMICAL CORPORATION, Beijing (CN); RESEARCH INSTITUTE OF PETROLEUM PROCESSING, SINOPEC, Beijing (CN)

(72) Inventors: Youhao Xu, Beijing (CN); Xin Wang, Beijing (CN); Yanfen Zuo, Beijing (CN); Shouye Cui, Beijing (CN); Xuhui Bai, Beijing (CN); Xinyu Xie, Beijing (CN)

(73) Assignees: CHINA PETROLEUM & CHEMICAL CORPORATION, Beijing (CN); RESEARCH INSTITUTE OF PETROLEUM PROCESSING, SINOPEC, Beijing (CN)

( * ) Notice: Subject to any disclaimer, the term of this patent is extended or adjusted under 35 U.S.C. 154(b) by 0 days.

(21) Appl. No.: 17/079,967

(22) Filed: Oct. 26, 2020

(65) Prior Publication Data
US 2021/0122987 A1  Apr. 29, 2021

(30) Foreign Application Priority Data
Oct. 24, 2019 (CN) .......................... 201911014993.7

(51) Int. Cl.
C10G 69/04 (2006.01)
C07C 4/06 (2006.01)
C10L 1/06 (2006.01)

(52) U.S. Cl.
CPC ................ *C10G 69/04* (2013.01); *C07C 4/06* (2013.01); *C10L 1/06* (2013.01);
(Continued)

(58) Field of Classification Search
CPC ............ C10G 69/04; C10G 2300/1074; C10G 2300/202; C10G 2300/206;
(Continued)

(56) References Cited

U.S. PATENT DOCUMENTS 3,891,540 A   6/1975  Demmel et al.
3,951,781 A   4/1976  Owen et al.
(Continued)

FOREIGN PATENT DOCUMENTS

CN    1004878 B    7/1989
CN    1078094 C    1/2002
(Continued)

OTHER PUBLICATIONS

Sinopec Research Institute of Petroleum Processing, English Translation of Chinese Patent CN101987972B, Aug. 2009, 11 pages.*

*Primary Examiner* — Thuan D Dang
(74) *Attorney, Agent, or Firm* — Novick, Kim & Lee, PLLC; Allen Xue (57) ABSTRACT

A process for producing propylene and a low-sulfur fuel oil component, comprising the steps of: i) contacting a hydrocarbon-containing feedstock oil with a catalytic conversion catalyst for reaction under effective conditions in a catalytic conversion reactor in the absence of hydrogen to obtain a reaction product comprising propylene; ii) separating the reaction product from step i) to obtain a catalytic cracking distillate oil, and iii) subjecting the catalytic cracking distillate oil to hydrodesulfurization to obtain a low-sulfur hydrogenated distillate oil suitable for use as a fuel oil component. The process can greatly improve the propylene
(Continued)

selectivity and propylene yield while producing more fuel oil components, significantly reduce the yield of dry gas and coke, and thus has better economic and social benefits.

15 Claims, 1 Drawing Sheet

(52) U.S. Cl.
CPC ............. *C10G 2300/1074* (2013.01); *C10G 2300/202* (2013.01); *C10G 2300/206* (2013.01); *C10G 2300/301* (2013.01); *C10G 2300/302* (2013.01); *C10G 2300/308* (2013.01); *C10G 2300/4006* (2013.01); *C10G 2300/4012* (2013.01); *C10G 2300/4018* (2013.01); *C10L 2270/023* (2013.01)

(58) Field of Classification Search
CPC ........ C10G 2300/301; C10G 2300/302; C10G 2300/308; C10G 2300/4006; C10G 2300/4012; C10G 2300/4018; C10G 11/05; C10G 45/08; C10G 2300/107; C10G 2300/1077; C10G 2300/70; C10G 2400/02; C10G 2400/20
See application file for complete search history.

(56) References Cited

U.S. PATENT DOCUMENTS

| | | | |
|---|---|---|---|
| 4,054,512 | A | 10/1977 | Dugan et al. |
| 4,940,529 | A | 7/1990 | Beaton et al. |
| 5,098,554 | A | 3/1992 | Krishna et al. |
| 5,192,421 | A | 3/1993 | Audeh et al. |
| 2007/0095724 | A1 | 5/2007 | Baptista et al. |
| 2011/0062054 | A1 | 3/2011 | Gao et al. |
| 2013/0048537 | A1* | 2/2013 | Noh ............... C10G 55/08 208/70 |
| 2016/0312130 | A1 | 10/2016 | Merdrignac et al. |

FOREIGN PATENT DOCUMENTS

| | | |
|---|---|---|
| CN | 101283074 A | 10/2008 |
| CN | 101531924 A | 9/2009 |
| CN | 101724431 A | 6/2010 |
| CN | 101987972 A | 3/2011 |
| CN | 102031138 A | 4/2011 |
| CN | 102373084 A | 3/2012 |
| CN | 102399585 A | 4/2012 |
| CN | 102746890 A | 10/2012 |
| CN | 103059954 A | 4/2013 |
| CN | 105623725 A | 6/2016 |
| CN | 109705913 A | 5/2019 |
| EP | 0940464 A2 | 9/1999 |
| WO | 2017116756 A1 | 7/2017 |

* cited by examiner

PROCESS FOR PRODUCING LIGHT OLEFINS AND LOW-SULFUR FUEL OIL COMPONENTS

CROSS REFERENCE TO RELATED APPLICATIONS

The present application claims the priority of the Chinese patent application No. 201911014993.7 filed on Oct. 24, 2019, titled "process for producing light olefins and low-sulfur fuel oil components", which is incorporated herein by reference in its entirety.

TECHNICAL FIELD

The application relates to the field of catalytic conversion of hydrocarbon oils, particularly to a process for catalytically converting hydrocarbon-containing feedstock oils into light olefins and low-sulfur fuel oil components.

BACKGROUND ART

With the rapid development of national economy, the problem of environmental pollution has received more and more attention, and environmental regulations are increasingly strict. According to the regulation, International Convention for the Prevention of Pollution from Ships, of International Maritime Organization (IMO), from Jan. 1, 2020, ships all over the world must use marine fuels with a sulfur content of no greater than 0.5%, and this will undoubtedly bring a huge revolution to the global market for marine fuels. According to BP prediction, global consumption of marine fuels in 2020 can reach about 3 hundred million tons, which will undoubtedly bring a huge challenge to the supply of low-sulfur fuel oils, and there is still a large gap between the supply capacity successively announced by main global petroleum processing enterprises and global market demand.

CN109722303A discloses a process for producing a blending component for low-sulfur marine fuels from high-sulfur heavy oils. The process comprises the steps of: a) feeding a high-sulfur heavy oil raw material into a visbreaking device for visbreaking to obtain a visbreaking residue; b) adding a composite modifier into the visbreaking residue obtained in the step a), and then subjecting the mixture to continuous settling to obtain an over flow at the upper part and a bottom flow at the lower part; and c) sending the over flow obtained in the step b) to a fixed bed residue hydrogenation device for hydrodesulfurization to obtain a blending component for low-sulfur marine fuels.

The quality of crude oils has become poorer as the production of crude oils increases, of which the main manifestations are the increases in density, viscosity, heavy metal content, sulfur content, nitrogen content, colloid content and asphaltene content of crude oils. At present, the price difference between inferior crude oils and high-quality crude oils is increasing as the shortage of petroleum resources becomes more and more serious. Producing as many high-value products as possible from inferior crude oils has brought a great challenge to traditional crude oil processing technology. However, the key to the processing of inferior crude oils is how to process the heaviest atmospheric residue fraction among crude oil fractions.

Catalytic cracking of residues is currently a key process for producing light olefins and high-octane gasoline in modern oil refineries, in which light cycle oil (LCO) is produced as a part of byproducts. Recently, LCO has been considered as a potential blending component for marine fuels. Although blending of a vacuum residue with LCO can produce a low-sulfur marine fuel, the proportion of LCO used as the fuel oil component cannot be too high due to the lower viscosity of LCO, and a simple blending of the two materials may result in layer separation during long-term storage since the distillation ranges of LCO and the vacuum residue do not overlap with each other. In addition, the hydrogen content of saturated hydrocarbons of vacuum residues is too high, and thus the use of vacuum residues as a fuel oil component may affect the economic benefit of enterprises.

With the rapid increase of the demand of derivatives such as polypropylene, the demand of propylene in China still exceeds the supply thereof, and the production of more propylene by catalytic cracking of heavy oils plays a more important role. As the price of marine fuels is lower than that of vehicle diesel oils, the production of marine fuels cannot provide good economic benefit. The production of a marine fuel along with high-value products, e.g. propylene and butylene, directing at the component characteristics of feedstock oil, has important significance.

In consideration of the current surplus oil refining capability in China, the developing of a process for producing more high-value propylene and providing low-sulfur marine fuel components by utilizing a core oil refining device, namely catalytic cracking device, is an important strategy for structural adjustment of oil refining industry, so that the requirements of improving the environmental protection standard and the market demand can be satisfied, and the enterprise competitiveness can be improved.

SUMMARY OF THE INVENTION

An object of the present application is to provide a catalytic conversion process for producing propylene and a low-sulfur fuel oil component, which can greatly improve propylene selectivity and propylene yield while producing more fuel oil components, and significantly reduce the yields of dry gas and coke, with good economic and social benefits.

To accomplish the above object, the present application provides a process for producing propylene and a low-sulfur fuel oil component, comprising the steps of:

i) contacting a hydrocarbon-containing feedstock oil with a catalytic conversion catalyst for reaction in a catalytic conversion reactor in the absence of hydrogen to obtain a reaction product comprising propylene;

ii) separating the reaction product from step i) to obtain a catalytic cracking distillate oil, wherein the catalytic cracking distillate oil has an initial boiling point of no less than about 200° C., a final boiling point of no greater than about 550° C., and a hydrogen content of no greater than about 12.0 wt %; and iii) subjecting the catalytic cracking distillate oil to hydrodesulfurization to obtain a low-sulfur hydrogenated distillate oil suitable for use as a fuel oil component, wherein the catalytic conversion catalyst comprises about 1-50 wt % zeolite, about 5-99 wt % inorganic oxide, and about 0-70 wt % clay, based on the total weight of the catalyst, the reaction conditions of step i) include: a reaction temperature of about 460-750° C., a weight hourly space velocity of about 10-100 $h^{-1}$ or a reaction time of about 1-10 seconds, and a catalyst-to-oil weight ratio of about 4-20.

Preferably, the reaction product obtained in step i) comprises about 8-25 wt % of propylene and about 15-50 wt % of the catalytic cracking distillate oil, relative to the weight of the hydrocarbon-containing feedstock oil.

The process of the present application can selectively crack alkanes, hydrocarbons with alkyl side group and the like present in the hydrocarbon-containing feedstock oil, produce propylene to the maximum extent, and simultaneously generate polycyclic aromatic hydrocarbons with short side chains that are retained in the catalytic cracking distillate oil suitable for use as a fuel oil component. By the process of the present application, the hydrocarbon-containing feedstock oil can be converted into propylene, butylene and a component for marine fuels, and the yield of dry gas and coke can be greatly reduced, so that effective utilization of petroleum resources can be realized.

Particularly, when compared with prior arts, the process of the present application provides at least one of the following benefits:

1. the propylene selectivity and propylene yield can be greatly improved while producing more fuel oil components, and thus some economic and social benefits can be achieved;

2. the yields of dry gas and coke can be markedly reduced while greatly increasing the production of high-value products such as propylene and the like; and 3. the total liquid yield can be significantly increased, so that the efficiency of utilization of petroleum resources can be improved.

BRIEF DESCRIPTION OF THE DRAWINGS

The drawings, forming a part of the present description, are provided to help the understanding of the present application, and should not be considered to be limiting. The present application can be interpreted with reference to the drawings in combination with the detailed description hereinbelow. In the drawings.

DETAILED DESCRIPTION OF THE INVENTION

The present application will be further described hereinafter in detail with reference to specific embodiments thereof and the accompanying drawings. It should be noted that the specific embodiments of the present application are provided for illustration purpose only, and are not intended to be limiting in any manner.

Any specific numerical value, including the endpoints of a numerical range, described in the context of the present application is not restricted to the exact value thereof, but should be interpreted to further encompass all values close to said exact value, for example all values within ±5% of said exact value. Moreover, regarding any numerical range described herein, arbitrary combinations can be made between the endpoints of the range, between each endpoint and any specific value within the range, or between any two specific values within the range, to provide one or more new numerical range(s), where said new numerical range(s) should also be deemed to have been specifically described in the present application.

Unless otherwise stated, the terms used herein have the same meaning as commonly understood by those skilled in the art; and if the terms are defined herein and their definitions are different from the ordinary understanding in the art, the definition provided herein shall prevail.

According to the present application, the term "catalytic cracking distillate oil" refers to a fraction having an initial boiling point of no less than about 200° C., preferably no less than about 250° C., and a final boiling point of no more than about 550° C., preferably no more than about 520° C., and most preferably no more than about 500° C. in the reaction product, i.e. a fraction having a distillation range of about 200-550° C., preferably about 250-520° C., more preferably about 250-500° C.

In the present application, the term "fluidized bed reactor", also referred to as "fluidized reactor", should be understood in its broadest sense, and covers all types of reactors that allow a gaseous feedstock to contact with solid catalyst particles in a fluidized state therein for a chemical reaction, including but not limited to dense bed, bubbling bed, boiling bed, turbulent bed, fast bed, gas phase transport bed (such as upflow fluidized bed and downflow fluidized bed, and the like. The fluidized bed reactor may be constant linear speed fluidized bed reactors, equal-diameter fluidized bed reactors, varied-diameter fluidized bed reactors, or the like, and may also be a composite reactor comprising two or more different types of fluidized beds connected in series or in parallel, such as a riser reactor or a composite reactor comprising a riser reactor in combination with a dense bed. Typically, the gas velocity of a dense bed may be in a range of about 0.1-2 m/s, while the gas velocity of a riser reactor may be in a range of about 1-30 m/s (excluding the catalyst).

In the context of the present application, in addition to those matters explicitly stated, any matter or matters not mentioned are considered to be the same as those known in the art without any change. Moreover, any of the embodiments described herein can be freely combined with another one or more embodiments described herein, and the technical solutions or ideas thus obtained are considered as part of the original disclosure or original description of the present application, and should not be considered to be a new matter that has not been disclosed or anticipated herein, unless it is clear to those skilled in the art that such a combination is obviously unreasonable.

All of the patent and non-patent documents cited herein, including but not limited to textbooks and journal articles, are hereby incorporated by reference in their entireties.

It has long been understood by those skilled in the art that the higher the conversion rate of heavy oil during catalytic cracking, the better. However, the inventors of the present application have found through creative thinking and repeated experiments that the conversion rate of heavy oil during catalytic cracking is not as high as possible, and when the conversion arrives at a certain degree, the increase of the desired product will be little, but the yield of the by-product dry gas and coke will be greatly increased. Therefore, the inventors have developed a mild catalytic cracking process based on the concept of selective cracking of alkane groups, in which the hydrocarbon feedstock is converted to a level within an optimal range, where the ratio of the total yield of dry gas and coke to the conversion rate is minimized, the propylene selectivity is good, polycyclic aromatic hydrocarbons difficult to be converted are retained in a fraction having a distillation range of 300-500° C. (called "catalytic gas oil") of the cracked product, and the generation of coke is limited to the greatest extent. Depending on the physicochemical properties of the catalytic gas oil, it can be used as an effective blending component for marine fuels.

Accordingly, the present application provides a process for producing propylene and a low-sulfur fuel oil component, comprising the steps of:

i) contacting a hydrocarbon-containing feedstock oil with a catalytic conversion catalyst for reaction under effective conditions in a catalytic conversion reactor in the absence of hydrogen to obtain a reaction product comprising propylene;

ii) separating the reaction product from step i) to obtain a catalytic cracking distillate oil, and iii) subjecting the catalytic cracking distillate oil to hydrodesulfurization to obtain a low-sulfur hydrogenated distillate oil, wherein the low-sulfur hydrogenated distillate oil can be used as a low-sulfur fuel oil component.

According to the present application, the hydrocarbon-containing feedstock oil may be selected from the group consisting of petroleum hydrocarbons, other mineral oils or mixtures thereof, in which the petroleum hydrocarbon may be selected from the group consisting of vacuum gas oils (VGOs), atmospheric gas oils, coker gas oils, deasphalted oils, vacuum residues (VRs), atmospheric residues, hydrogenated heavy oils or any mixtures thereof, and said other mineral oil may be selected from the group consisting of coal liquefied oils, tar sand oils, shale oils or any mixtures thereof.

According to the present application, the catalytic conversion reactor may be selected from various types of fluidized bed reactors, such as a single fluidized bed reactor, or a composite reactor comprising a plurality of fluidized bed reactors connected in series or in parallel. In certain preferred embodiments, the fluidized bed reactor may be an equal-diameter riser reactor or various types of varied-diameter fluidized bed reactors, such as the reactor disclosed in Chinese Patent No. CN 1078094C.

According to the present application, the catalytic conversion catalyst may comprise about 1-50 wt % zeolite, about 5-99 wt % inorganic oxide, and about 0-70 wt % clay, based on the total weight of the catalyst. Preferably, the catalyst may comprise about 5-45 wt % zeolite, more preferably about 10-40 wt % zeolite, about 5-80 wt % inorganic oxide and about 10-70 wt % clay.

In a preferred embodiment, the zeolite may comprise about 51-100 wt %, preferably about 70-100 wt %, of a mesoporous zeolite and about 0-49 wt %, preferably about 0-30 wt %, of a macroporous zeolite, based on the total weight of the zeolite. Preferably, the mesoporous zeolite has a silica-alumina ratio of greater than about 10, preferably greater than about 50, more preferably greater than about 100. The mesoporous zeolite is preferably selected from the group consisting of ZSM-type zeolites and ZRP zeolites; the macroporous zeolite is preferably a Y-type zeolite. Optionally, the zeolite may be modified with a non-metallic element such as phosphorus and the like and/or a transition metal element such as iron, cobalt, nickel and the like. The inorganic oxide is preferably selected from the group consisting of silica, alumina, and combinations thereof; and the clay is preferably selected from kaolin and/or halloysite.

According to the present application, the "effective conditions" refer to conditions that enable the hydrocarbon-containing feedstock to undergo a catalytic conversion reaction to obtain a reaction product comprising propylene and catalytic cracking distillate oil, preferably comprising about 8-25 wt % propylene and about 15-50 wt % catalytic cracking distillate oil, relative to the weight of the hydrocarbon-containing feedstock oil. In a preferred embodiment, the reaction conditions of the catalytic conversion step i) include: a reaction temperature of about 460-750° C., preferably about 480-700° C., more preferably about 480-600° C., and most preferably about 500-560° C.; a weight hourly space velocity (e.g., for a dense bed reactor, a fast bed reactor, etc.) of about 5-100 h$^{-1}$, preferably about 10-70 h$^{-1}$, more preferably about 15-50 h$^{-1}$, and most preferably about 18-40 h$^{-1}$ or a reaction time (e.g., for a riser reactor) of about 1-10 seconds, preferably about 1.5-10 seconds, more preferably about 2.0-8.0 seconds, and most preferably about 4-8 seconds; and a catalyst-to-oil weight ratio of about 1-30, preferably about 5-15, and more preferably about 5-10.

In a preferred embodiment, the step i) is carried out to such an extent that the resulting reaction product has a propylene/propane mass ratio of no less than about 4, preferably no less than about 6, most preferably no less than about 8; and/or an isobutene/isobutane mass ratio of no less than about 1, preferably no less than about 1.5, most preferably no less than about 1.8.

In a preferred embodiment, the step i) is carried out to such an extent that the yield of the catalytic cracking distillate oil in the resulting reaction product is not less than about 15%, preferably not less than about 20%, more preferably not less than about 25%, and not more than about 50%, relative to the weight of said hydrocarbon-containing feedstock oil.

As is well known to those skilled in the art, the conversion rate of feedstock oil in a catalytic conversion process is typically expressed as the sum of the yields of gas, gasoline and coke. In the process of the present application, the end products of the catalytic conversion process include only dry gas, liquefied gas, gasoline, catalytic cracking distillate oil and coke. Thus, in the present application, the conversion rate of the feedstock oil is substantially equal to 100% minus the yield of the catalytic cracking distillate oil. In turn, the conversion rate of the catalytic conversion process according to the present application is controlled to a level of no greater than about 85%, preferably no greater than about 80%, and most preferably no greater than about 75%, and no less than about 50%.

In certain preferred embodiments, the process further comprises a step of separating the reaction product of step i) from the spent catalyst, wherein the spent catalyst is recycled to the reactor after stripping and regeneration by coke burning, and wherein the separated reaction product comprises propylene, gasoline and the catalytic cracking distillate oil. Methods for separating materials such as propylene from the reaction product are well known to those skilled in the art and will not be described in detail herein.

In a preferred embodiment, a catalyst comprising a Group VIB metal and/or a Group VIII metal supported on an alumina and/or amorphous silica-alumina carrier is used in the hydrodesulfurization step iii). Further preferably, the catalyst used in the hydrodesulfurization step iii) comprises about 0-10 wt % of an additive, about 1-40 wt % of at least one Group VIII metal (calculated as metal oxide), and about 1-50 wt % of at least one Group VIB metal (calculated as metal oxide), with the balance being a carrier selected from alumina and amorphous silica-alumina, wherein the additive comprises a non-metallic element selected from fluorine, phosphorus, and the like, a metallic element selected from titanium, platinum, and the like, or a combination thereof. For example, the additive may be a phosphorus-containing auxiliary or a fluorine-containing auxiliary, such as ammonium fluoride. The Group VIB metal is preferably selected from molybdenum, tungsten or a combination thereof; and the Group VIII metal is preferably selected from nickel, cobalt or a combination thereof.

In a preferred embodiment, the conditions of the hydrodesulfurization step iii) include: a reaction pressure of about 2.0-24.0 MPa, preferably about 3.0-15.0 MPa; a reaction temperature of about 200-500° C., preferably about 300-400° C.; a hydrogen-to-oil volume ratio of about 50-5000 Nm³/m³, preferably about 200-2000 Nm³/m³; and a liquid hourly space velocity of about 0.1-30.0 h$^{-1}$, preferably about 0.2-10.0 h$^{-1}$.

According to the present application, the catalytic cracking distillate oil has an initial boiling point of no less than about 200° C., a final boiling point of no greater than about 550° C., and a hydrogen content of no greater than about 12.0 wt %; preferably, the catalytic cracking distillate oil has an initial boiling point of no less than about 250° C., a final boiling point of no greater than about 520° C., more preferably no greater than about 500° C., and a hydrogen content of no greater than about 11.5 wt %.

In a preferred embodiment, the low-sulfur hydrogenated distillate oil obtained via the hydrodesulfurization of the catalytic cracking distillate oil has a sulfur content of no greater than about 0.1%, preferably no greater than about 0.05%, and is used as a blending component for fuel oils.

A particular embodiment of the process according to the present application is described below with reference to FIG. 1.

A pre-lifting medium is introduced into the bottom of a varied-diameter fluidized bed reactor 2 (such as the reactor disclosed in Chinese Patent No. CN 1078094C) through a pipeline 1, a regenerated catalyst from a regenerated catalyst sloped pipe 16 moves upwards along the reactor under the action of the pre-lifting medium, and a feedstock oil is fed into the bottom of a first reaction zone 8 of the varied-diameter fluidized bed reactor 2 through a pipeline 3 together with an atomized steam from a pipeline 4 to be mixed with the existing stream in the reactor. The feedstock oil is cracked on the hot catalyst and moves upwards into a second reaction zone 9 of the varied-diameter fluidized bed reactor 2 for further reaction. The resulting oil gas and inactivated spent catalyst are passed to a cyclone separator in a disengager 7 to accomplish the separation of the spent catalyst and the oil gas. The oil gas is passed to a main oil gas pipeline 17, and fine powders of the catalyst are returned to the disengager 7 through a dipleg of the cyclone separator. The spent catalyst in the disengager 7 is passed to a stripping section 10 and is contacted with a stripping steam from a pipeline 11. The oil gas stripped from the spent catalyst is passed through the cyclone separator into the main oil gas pipeline 17. The stripped spent catalyst is sent to a regenerator 13 through a spent catalyst sloped pipe 12, and a main air is introduced into the regenerator through a pipeline 14 to burn out the coke deposited on the spent catalyst, so that the inactivated spent catalyst can be regenerated. A flue gas is discharged through a pipeline 15. The regenerated catalyst is recycled to the varied-diameter fluidized bed reactor 2 through the regenerated catalyst sloped pipe 16 for reuse.

The oil gas is passed to a subsequent fractionation unit 18 through the main oil gas pipeline 17, and after separation, the dry gas obtained is discharged through a pipeline 19; the liquefied gas obtained is discharged through a pipeline 20, and is separated into propylene, propane and C4 hydrocarbons in a gas separation unit 25, and the propylene, propane and C4 hydrocarbons are discharged through pipelines 26, 27 and 28 respectively; the gasoline obtained is discharged through a pipeline 21; the light cycle oil fraction obtained having a distillation range of 200-250° C. is withdrawn through a pipeline 22 and then recycled to the middle-upper part of the first reaction zone 8 of the varied-diameter fluidized bed reactor 2 through a pipeline 31 together with an atomized steam from a pipeline 32; the slurry oil obtained is withdrawn through a pipeline 24 and recycled to the first reaction zone 8 of the varied-diameter fluidized bed reactor 2 (optionally passed into the first reaction zone 8 together with the feedstock oil from the pipeline 3 through a feedstock nozzle) for refining so as to recover fine powders of the catalyst; the catalytic cracking distillate oil obtained is passed to a hydrotreating unit 29 through a pipeline 23, and the hydrogenated distillate oil obtained after the hydrotreatment is discharged through a pipeline 30. The distillation range and the processing scheme of each fraction can be adjusted according to the actual needs of a refinery, for example, the gasoline may be split to obtain a light gasoline fraction, and the light gasoline fraction may be recycled to the second reaction zone 9 of the varied-diameter fluidized bed reactor 2 through a pipeline 6 together with an atomized steam from a pipeline 5 for refining to increase the yield of propylene.

In certain preferred embodiments, the present application provides the following technical solutions:

1. A process for producing light olefins (especially propylene) and a low-sulfur fuel oil component comprises contacting a feedstock oil with a catalyst for reaction in a catalytic conversion reactor at a temperature, a weight hourly space velocity and a weight ratio of catalyst to feedstock oil sufficient to produce a reaction product comprising 8-25 wt % of propylene and 15-50 wt % of catalytic cracking distillate oil, and subjecting the catalytic cracking distillate oil to hydrodesulfurization to obtain a low-sulfur hydrogenated distillate oil suitable for use as a fuel oil component.

2. The process according to Item 1, wherein the feedstock oil is selected from the group consisting of petroleum hydrocarbons selected from vacuum gas oils, atmospheric gas oils, coker gas oils, deasphalted oils, vacuum residues, atmospheric residues, hydrogenated heavy oils or a mixture of two or more thereof, and/or other mineral oils selected from coal liquefied oils, tar sand oils, shale oils or a mixture of two or more thereof.

3. The process according to Item 1, wherein the catalytic conversion reactor is selected from the group consisting of a riser reactor, a constant linear speed fluidized bed, an equal-diameter fluidized bed, an upflow conveyor line, a downflow conveyor line, or a combination of two or more thereof, or a combination of two or more reactors of the same type, including a combination of reactors connected in series and/or in parallel, wherein the riser reactor is a conventional equal-diameter riser reactor or various types of varied-diameter fluidized beds.

4. The process according to Item 1, wherein the catalytic conversion catalyst comprises 1-50 wt % of zeolite, 5-99 wt % of inorganic oxide and 0-70 wt % of clay, based on the total weight of the catalyst, in which the zeolite is mesoporous zeolite and optionally macroporous zeolite, in which the mesoporous zeolite accounts for 51-100 wt % of the total weight of the zeolite, the mesoporous zeolite has a silica-alumina ratio of greater than 50, preferably greater than 80, and the macroporous zeolite accounts for 0-49 wt % of the total weight of the zeolite.

5. The process according to Item 1, wherein the conditions for the catalytic conversion include: a reaction temperature of 460-750° C., a weight hourly space velocity of 10-100 h$^{-1}$, and a weight ratio of the catalyst to the catalytic conversion feedstock oil of 4-20.

6. The process according to Item 5, wherein the conditions for the catalytic conversion include: a reaction temperature of 480-700° C., a weight hourly space velocity of 30-80 h$^{-1}$, and a weight ratio of the catalyst to the catalytic conversion feedstock oil of 5-12.

7. The process according to Item 1, wherein the catalytic cracking distillate oil has an initial boiling point of no less than 200° C. and a hydrogen content of no more than 12.0 wt %.

8. The process according to Item 7, wherein the catalytic cracking distillate oil has an initial boiling point of no less than 250° C. and a hydrogen content of no more than 11.5 wt %.

9. The process according to Item 1, wherein a catalyst comprising a Group VIB metal and/or a Group VIII metal supported on an alumina and/or amorphous silica-alumina carrier is used for the hydrodesulfurization.

10. The process according to Item 9, wherein the catalyst for hydrodesulfurization consists of 0-10 wt % of an additive, 1-40 wt % of one or more Group VIII metals, 1-50 wt % of one or more Group VIB metals, and a balance amount of alumina and/or amorphous silica-alumina carrier, wherein the additive is selected from the group consisting of non-metallic elements such as fluorine, phosphorus, and the like, and metallic elements such as titanium, platinum, and the like.

11. The process according to Item 1, wherein the hydrodesulfurization conditions include: a reaction pressure of 2.0-24.0 MPa, a reaction temperature of 200-500° C., a hydrogen-to-oil volume ratio of 50-5000 $Nm^3/m^3$, and a liquid hourly space velocity of 0.1-30.0 $h^{-1}$.

12. The process according to Item 11, wherein the hydrodesulfurization conditions include: a reaction pressure of 3.0-15.0 MPa; a reaction temperature of 300-400° C.; a hydrogen-to-oil volume ratio of 200-2000 $Nm^3/m^3$; a liquid hourly space velocity of 0.2-10.0 $h^{-1}$.

13. The process according to Item 1, wherein the sulfur content in the hydrogenated distillate oil of step (3) is not more than 0.1%, preferably not more than 0.05%.

EXAMPLES

The present application will be further described with reference to the following examples, but is not limited thereto.

Properties of the feedstock oil and the catalyst used in the following examples and comparative examples are shown in Tables 1 and 2, respectively. The catalytic conversion catalyst used in the comparative examples was MMC-1, a catalyst manufactured by Qilu Branch of Sinopec Catalyst Co., Ltd.

The hydrogen content of the catalytic cracking distillate oil obtained in each example is measured by a carbon and hydrogen analysis meter according to the NB/SH/T 0656-2017 standard.

The catalytic conversion catalyst used in the examples was prepared as follows:

969 g of halloysite (available from China Kaolin clay Co., Ltd., with solid content of 73%) was slurried in 4300 g of decationized water, 781 g of pseudo-boehmite (available from Shandong Zibo Bauxite Plant, with solid content of 64%) and 144 ml of hydrochloric acid (with concentration of 30% and specific gravity of 1.56) were added and stirred evenly. The mixture was kept still and aged for 1 hour at 60° C., the pH value was kept at 2-4, and then the mixture was cooled to room temperature. 5000 g of a pre-prepared slurry comprising 1600 g of a mesoporous shape-selective ZSM-5 zeolite (available from Qilu Branch of Sinopec Catalyst Co., Ltd.) containing chemical water and having a silica-alumina ratio higher than 150 was added and stirred evenly, and the resultant was spray dried and washed off free $Na^+$ to obtain a catalyst. The catalyst obtained was aged at 800° C. with 100% steam, and the aged catalyst was designated as catalyst A, of which the properties are shown in Table 2.

The hydrodesulfurization catalyst used in the examples was prepared as follows:

1000 g of pseudo-boehmite produced by ChangLing Branch of Sinopec Catalyst Co., Ltd. was weighed, and 1000 ml of an aqueous solution containing 10 ml of nitric acid (chemically pure) was then added. The mixture was shaped by band extrusion on a double-screw extruder, dried at 120° C. for 4 hours, and calcined at 800° C. for 4 hours to obtain a catalyst carrier. The carrier was immersed in 900 ml of an aqueous solution containing 120 g of ammonium fluoride for 2 hours, dried at 120° C. for 3 hours, and calcined at 600° C. for 3 hours; after cooling to room temperature, the resultant was further immersed in 950 ml of an aqueous solution containing 133 g of ammonium metamolybdate for 3 hours, dried at 120° C. for 3 hours, and calcined at 600° C. for 3 hours; and after cooling to room temperature again, the resultant was finally immersed in 900 ml of an aqueous solution containing 180 g of nickel nitrate and 320 g of ammonium metatungstate for 4 hours, dried at 120° C. for 3 hours and calcined at 600° C. for 4 hours to produce a catalyst B.

TABLE 1

Properties of the feedstock oil used in the examples and comparative examples

| | Name of the feedstock oil | | |
|---|---|---|---|
| | VGO + 30% VR-1 | Hydrogenated heavy oil | VGO |
| Density (20° C.), $g/cm^3$ | 0.8905 | 0.963 | 0.8597 |
| Carbon residue, wt % | 2.94 | 8.0 | 0.07 |
| Element/wt % | | | |
| Carbon | 86.48 | 87.28 | 85.63 |
| Hydrogen | 13.18 | 11.63 | 13.45 |
| Sulfur | 0.15 | 0.4 | 0.06 |
| Nitrogen | 0.19 | 0.2 | 0.08 |
| Four-component analysis/wt % | | | |
| Saturates | 64.5 | 49.4 | 86.6 |
| Aromatics | 24.2 | 37.3 | 13.4 |
| Resins | 11.1 | 11.4 | 0.0 |
| Asphaltenes | 0.2 | 1.9 | 0.0 |

TABLE 2

Properties of the catalytic conversion catalysts used in the examples and comparative examples

| Name of the catalyst | A | MMC-1 |
|---|---|---|
| Chemical composition/wt % | | |
| $Al_2O_3$ | 49.2 | 50.2 |
| $Na_2O$ | 0.07 | 0.052 |
| Physical Properties | | |
| Specific surface area/($m^2 \cdot g^{-1}$) | / | 115 |
| Bulk density/($g \cdot cm^{-3}$) | 0.79 | 0.80 |
| Abrasion index/(% $\cdot h^{-1}$) | 1.1 | 2.8 |
| Sieve composition/wt % | | |
| 0-40 μm | 14.2 | 15.8 |
| 0-80 μm | 53.8 | 75.5 |
| 0-105 μm | / | 90.5 |
| 0-149 μm | 89.5 | / |

Example 1-a

Figure 1:
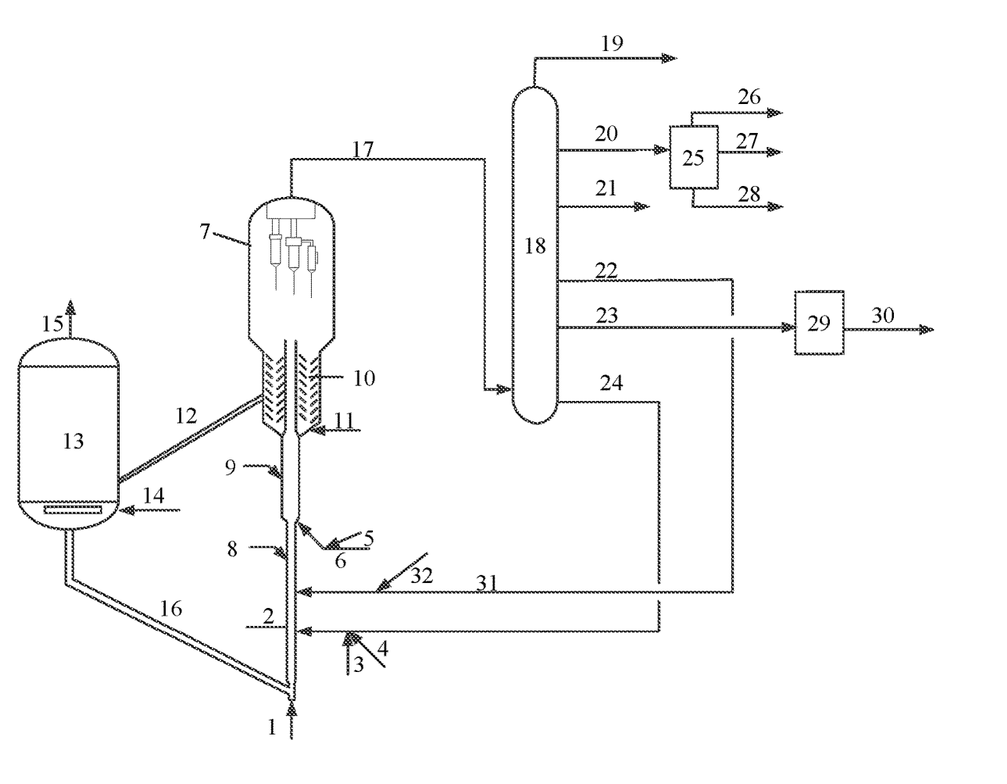
FIG. 1 is a schematic flow diagram of a preferred embodiment of the process for producing propylene and a low-sulfur fuel oil component of the present application.

This example was carried out in accordance with the process scheme shown in FIG. 1, using VGO+30% VR-1 as a feedstock oil, and the catalyst A as a catalytic conversion catalyst, on a medium-sized catalytic cracking unit comprising a varied-diameter fluidized bed reactor. The resulting oil gas and spent catalyst were separated in a disengager, and the oil gas product was split into propylene, butylene, gasoline and a catalytic cracking distillate oil (with a distillation range of 250-500° C., and a hydrogen content of 11.2 wt %) according to the distillation ranges of those fractions in a fractionation unit. The reaction conditions and product distribution are listed in Table 3.

The catalytic cracking distillate oil obtained was sent to a hydrodesulfurization reactor together with hydrogen to contact with the hydrodesulfurization catalyst B, and react under a reaction pressure of 6.0 MPa, a reaction temperature of 350° C., a hydrogen-to-oil volume ratio of 350 and a liquid hourly space velocity of 2.0 $h^{-1}$ to obtain a low-sulfur hydrogenated distillate oil. The low-sulfur hydrogenated distillate oil was used as a fuel oil component and blended with another fuel oil component "vacuum residue VR-2", to obtain a RMG 380 fuel oil product satisfying the National Standard GB 17411-2015, Marine Fuel Oils, of which the properties are shown in Table 4.

Example 1-b

This example was carried out in accordance with the process scheme shown in FIG. 1, using VGO as a feedstock oil, and the catalyst A as a catalytic conversion catalyst, on a medium-sized catalytic cracking unit comprising a varied-diameter fluidized bed reactor. The resulting oil gas and spent catalyst were separated in a disengager, and the oil gas product was split into propylene, butylene, gasoline and a catalytic cracking distillate oil (with a distillation range of 250-500° C., and a hydrogen content of 11.3 wt %) according to the distillation ranges of those fractions in a fractionation unit. The reaction conditions and product distribution are listed in Table 3.

Example 1-c

This example was carried out in accordance with the process scheme shown in FIG. 1, using VGO+30% VR-1 as a feedstock oil and the catalyst A as a catalytic conversion catalyst, on a medium-sized catalytic cracking unit comprising an equal-diameter riser reactor. The resulting oil gas and spent catalyst were separated in a disengager, and the oil gas product was split into propylene, butylene, gasoline and a catalytic cracking distillate oil (with a distillation range of 250-500° C., and a hydrogen content of 11.2 wt %) according to the distillation ranges of those fractions in a fractionation unit. The reaction conditions and product distribution are listed in Table 3.

Comparative Example 1

This comparative example was carried out in accordance with the conventional deep catalytic cracking process described in CN1004878B, using VGO as a feedstock oil, and the catalyst MMC-1 as a catalytic cracking catalyst, on a medium-sized unit comprising a riser reactor in combination with a dense-phase fluidized bed. The resulting oil gas and spent catalyst were separated in a disengager, and the product was split into propylene, butylene, gasoline and a light cycle oil (with a distillation range of 200-350° C., and a hydrogen content of 9.8 wt %) according to the distillation ranges of those fractions in a fractionation unit. The reaction conditions and product distribution are listed in Table 3.

Example 2

This example was carried out in accordance with the process scheme shown in FIG. 1, using the hydrogenated heavy oil as a feedstock oil, and the catalyst A as a catalytic conversion catalyst, on a medium-sized catalytic cracking unit comprising a varied-diameter fluidized bed reactor. The resulting oil gas and spent catalyst were separated in a disengager, and the oil gas product was split into propylene, butylene, gasoline and a catalytic cracking distillate oil (with a distillation range of 250-500° C., and a hydrogen content of 10.9 wt %) according to the distillation ranges of those fractions in a fractionation unit. The reaction conditions and product distribution are listed in Table 3.

The catalytic cracking distillate oil obtained was sent to a hydrodesulfurization reactor together with hydrogen to contact with the hydrodesulfurization catalyst B, and react under a reaction pressure of 9.0 MPa, a reaction temperature of 330° C., a hydrogen-to-oil volume ratio of 650 and a liquid hourly space velocity of 8.0 $h^{-1}$ to obtain a low-sulfur hydrogenated distillate oil. The low-sulfur hydrogenated distillate oil was used as a fuel oil component and blended with another fuel oil component "vacuum residue VR-3", to obtain a RMG 180 fuel oil product satisfying the National Standard GB 17411-2015, Marine Fuel Oils, of which the properties are shown in Table 5.

TABLE 3

Reaction conditions and product distributions of the examples and comparative examples

| Ex./Comp. Ex. | Ex. 1-a | Ex. 1-b | Ex. 1-c | Ex. 2 | Comp. Ex. 1 |
|---|---|---|---|---|---|
| Feedstock oil | VGO + 30% VR-1 | VGO | VGO + 30% VR-1 | Hydrogenated heavy oil | VGO |
| Type of reactor | Varied-diameter fluidized bed | Varied-diameter fluidized bed | Equal-diameter riser reactor | Varied-diameter fluidized bed | Riser reactor + dense-phase fluidized bed |
| Temperature of first reaction zone/° C. | 530 | 530 | 530 (reaction temperature, ° C.) | 530 | 580 |
| Time in first reaction zone, s | 1.2 (WHSV of about 95 $h^{-1}$) | 1.2 (WHSV of about 95 $h^{-1}$) |  | 1.2 (WHSV of about 95 $h^{-1}$) | 1.2 (WHSV of about 95 $h^{-1}$) |
| Temperature of second reaction zone/° C. | 520 | 520 | 3.5 (reaction time, s) | 520 | 580 (dense-phase fluidized bed) |

TABLE 3-continued

Reaction conditions and product distributions of the examples and comparative examples

| Ex./Comp. Ex. | Ex. 1-a | Ex. 1-b | Ex. 1-c | Ex. 2 | Comp. Ex. 1 |
|---|---|---|---|---|---|
| Space velocity in second reaction zone/$h^{-1}$ | 30 | 30 | | 30 | 4 (dense-phase fluidized bed) |
| Catalyst-to-oil ratio | 6 | 6 | 6 | 6 | 10 |
| Product distribution/wt % | | | | | |
| Dry gas | 2.12 | 1.82 | 2.35 | 1.83 | 11.97 |
| Liquefied gas | 32.10 | 33.40 | 32.80 | 30.79 | 42.91 |
| Gasoline | 32.51 | 33.51 | 31.85 | 31.83 | 28.33 |
| Light cycle oil | / | / | / | / | 10.94 |
| Catalytic cracking distillate oil | 29.32 | 27.73 | 28.32 | 31.29 | / |
| Coke | 3.95 | 3.54 | 4.68 | 4.26 | 5.85 |
| Total | 100.00 | 100.00 | 100.00 | 100.00 | 100.00 |
| Conversion* | 70.68 | 72.27 | 71.68 | 68.71 | 89.06 |
| Propylene yield/wt % | 14.42 | 15.00 | 13.45 | 10.89 | 19.07 |
| Propylene/propane mass ratio | 8.10 | 8.20 | 8.00 | 8.00 | 6.2 |
| Isobutene/isobutane mass ratio | 1.85 | 1.85 | 1.80 | 1.80 | 0.1 |
| Total liquid yield/wt % | 93.93 | 94.64 | 92.97 | 94.01 | 82.18 |

*Conversion = dry gas yield + liquefied gas yield + gasoline yield + coke yield.

As can be seen from the results of Table 3, when compared to Comparative Example 1, Example 1-a and Example 1-c can provide not only propylene yields of as high as 14.42 wt % and 13.45 wt %, respectively, but also catalytic cracking distillate oil yields of as high as 29.32 wt % and 28.32 wt %, respectively, with the yields of dry gas and coke being markedly reduced, and the total liquid yield being significantly increased, using a feedstock oil that is more inferior; while Example 1-b can provide a propylene yield of as high as 15.00 wt % and a catalytic cracking distillate oil yield of 27.73 wt %, with the yields of dry gas and coke being markedly reduced and the total liquid yield being significantly increased, using the same feedstock oil.

TABLE 4

Properties of the low-sulfur hydrogenated distillate oil and fuel oil product obtained in Example 1-a

| | Component name | | | |
|---|---|---|---|---|
| | Fuel oil component 1 Low-sulfur hydrogenated distillate oil | Fuel oil component 2 Vacuum residue VR-2 | RMG 380 fuel oil product | Standard for RMG 380 fuel oil |
| Blend ratio/% (w) | 40 | 60 | | |
| Viscosity (50° C.)/($mm^2$/s) | 9.8 | 2978.6 | 214.2 | ≯380 |
| Density (15° C.)/(kg/$m^3$) | 927.5 | 1012.7 | 980.4 | ≯991.0 |
| Density (20° C.)/(kg/$m^3$) | 926.2 | 1008.2 | 977.1 | ≯987.6 |
| Calculated carbon aromaticity index (CCAI) | 844.9 | 855.4 | 847.5 | ≯870 |
| Sulfur content/% (w) | 0.05 | 0.77 | 0.50 | ≯0.5 |
| Total acid value/(mgKOH/g) | 0.07 | 0.77 | 0.50 | ≯2.5 |
| Carbon residue/% (w) | 0.00 | 17.2 | 10.66 | ≯18.0 |

TABLE 5

Properties of the low-sulfur hydrogenated distillate oil and fuel oil product obtained in Example 2

| | Component name | | | |
|---|---|---|---|---|
| | Fuel oil component 1 Hydrogenated distillate oil | Fuel oil component 2 Vacuum residue VR-3 | RMG 180 fuel oil product | Standard for RMG 180 fuel oil |
| Blend ratio/% (w) | 38 | 62 | | |
| Viscosity (50° C.)/(mm²/s) | 9.6 | 2000.7 | 135 | ≯180 |
| Density (15° C.)/(kg/m³) | 926.4 | 1003.8 | 974.0 | ≯991.0 |
| Density (20° C.)/(kg/m³) | 925.3 | 1000.3 | 971.8 | ≯987.6 |
| Calculated carbon aromaticity index (CCAI) | 843.3 | 849.6 | 846.6 | ≯870 |
| Sulfur content/% (w) | 0.04 | 0.71 | 0.46 | ≯0.5 |
| Total acid value/(mgKOH/g) | 0.06 | 0.72 | 0.47 | ≯2.5 |
| Carbon residue/% (w) | 0.00 | 15.6 | 9.67 | ≯18.0 |

Preferred embodiments of the present application have been described in detail hereinabove, but the present application is not limited to the details of those embodiments. Various modifications may be made without departing from the spirit of the present application, and these modifications also fall within the scope of the present application.

It should be noted that the various technical features described in the above embodiments can be combined in any suitable manner without contradiction. For brevity, various possible combinations are not described separately in the present application, but such combinations also fall within the scope of the present application.

In addition, various embodiments of the present application can be combined in any manner as long as it does not depart from the spirit of the present application, and such combinations should be considered as a part of the disclosure of the present application.

What is claimed:

1. A process for producing propylene and a low-sulfur fuel oil component, comprising the steps of:
   i) contacting a hydrocarbon-containing feedstock oil with a catalytic conversion catalyst for reaction in a catalytic conversion reactor in the absence of hydrogen under conditions including a reaction temperature of 500-560° C., a weight hourly space velocity of 18-40 h$^{-1}$ or a reaction time of 4-8 seconds, and a catalyst-to-oil weight ratio of 5-10 till a conversion rate of 50-75% to obtain a reaction product comprising propylene;
   ii) separating the reaction product from step i) to obtain a catalytic cracking distillate oil and propylene, wherein the catalytic cracking distillate oil has an initial boiling point of no less than 200° C., a final boiling point of no greater than 550° C., and a hydrogen content of no greater than 12.0 wt %, wherein a weight percentage of propylene is 8-25 wt % and a weight percentage of the catalytic cracking distillate oil is 25-50 wt %, relative to a weight of the hydrocarbon-containing feedstock oil;
   iii) subjecting the catalytic cracking distillate oil to hydrodesulfurization to obtain a low-sulfur hydrogenated distillate oil having a sulfur content of no greater than 0.1%; and
   iv) outputting the low-sulfur hydrogenated distillate oil and using the outputted low-sulfur hydrogenated distillate oil as a fuel oil component for fuel oil blending, wherein the catalytic conversion catalyst comprises about 1-50 wt % zeolite, about 5-99 wt % inorganic oxide, and about 0-70 wt % clay, based on the total weight of the catalyst.

2. The process according to claim 1, wherein in said catalytic conversion catalyst, said zeolite comprises 51-100 wt % mesoporous zeolite and 0-49 wt % macroporous zeolite, based on the total weight of the zeolite, wherein said mesoporous zeolite has a silica-alumina ratio of greater than 10.

3. The process according to claim 2, wherein step i) is carried out to such an extent that the resulting reaction product has a propylene/propane mass ratio of no less than 6; and/or an isobutene/isobutane mass ratio of no less than 1.5.

4. The process according to claim 2, wherein the mesoporous zeolite is selected from the group consisting of ZSM zeolites and ZRP zeolites; and the macroporous zeolite is a Y zeolite.

5. The process according to claim 1, wherein step i) is carried out to such an extent that the resulting reaction product has a propylene/propane mass ratio of no less than about 4; and/or an isobutene/isobutane mass ratio of no less than about 1.

6. The process according to claim 1, wherein step i) is carried out to such an extent that the yield of the catalytic cracking distillate oil is about 27-32 wt %, relative to the weight of said hydrocarbon-containing feedstock oil.

7. The process according to claim 1, wherein the hydrocarbon-containing feedstock oil is selected from the group consisting of petroleum hydrocarbons, other mineral oils or mixtures thereof, wherein the petroleum hydrocarbon is selected from the group consisting of vacuum gas oils, atmospheric gas oils, coker gas oils, deasphalted oils, vacuum residues, atmospheric residues, hydrogenated heavy oils, and mixtures thereof, and said other mineral oil is selected from the group consisting of coal liquefied oils, tar sand oils, shale oils, and mixtures thereof.

8. The process according to claim 1, wherein the catalytic conversion reactor is a single fluidized bed reactor or a composite reactor comprising a plurality of fluidized bed reactors connected in series or in parallel.

9. The process according to claim 1, wherein said catalytic cracking distillate oil has an initial boiling point of no less than 250° C., a final boiling point of no greater than 520° C., and a hydrogen content of no greater than 11.5 wt %.

10. The process according to claim 1, wherein the hydrodesulfurization step iii) is carried out in presence of a hydrodesulfurization catalyst comprising a Group VIB metal and/or a Group VIII metal supported on an alumina and/or amorphous silica-alumina carrier.

11. The process according to claim 10, wherein the hydrodesulfurization catalyst comprises an additive, 1-40 wt % of at least one Group VIII metal (calculated as metal oxide), and about 1-50 wt % of at least one Group VIB metal (calculated as metal oxide), wherein the additive is a phosphorus-containing compound, a fluorine-containing compound, or a mixture thereof.

12. The process according to claim 1, wherein the conditions of the hydrodesulfurization step iii) include: a reaction pressure of about 2.0-24.0 MPa, a reaction temperature of about 200-500° C., a hydrogen-to-oil volume ratio of about 50-5000 $Nm^3/m^3$, and a liquid hourly space velocity of about 0.1-30.0 $h^{-1}$.

13. The process according to claim 1, wherein the hydrogenated distillate oil obtained in step iii) has a sulfur content of no greater than 0.05%.

14. The process according to claim 1, wherein, in step i), the weight percentage of the catalytic cracking distillate oil is 27-32 wt % and the weight of propylene is 10-15 wt %, relative to the weight of said hydrocarbon-containing feedstock oil.

15. The process according to claim 1, wherein step i) is carried out to such an extent that the resulting reaction product has a propylene/propane mass ratio of no less than 8; and/or an isobutene/isobutane mass ratio of no less than 1.8.

* * * * *